United States Patent
Smith

(10) Patent No.: US 10,350,241 B2
(45) Date of Patent: *Jul. 16, 2019

(54) TRACE ELEMENTS

(71) Applicant: Warburton Technology Limited, Dublin (IE)

(72) Inventor: William Alfred Smith, Dublin (IE)

(73) Assignee: Warburton Technology Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/968,866

(22) Filed: May 2, 2018

(65) Prior Publication Data

US 2018/0250334 A1 Sep. 6, 2018

Related U.S. Application Data

(60) Continuation of application No. 15/660,439, filed on Jul. 26, 2017, now abandoned, which is a division of application No. 13/130,336, filed as application No. PCT/IB2009/055402 on Nov. 30, 2009, now Pat. No. 9,750,764.

(30) Foreign Application Priority Data

Dec. 9, 2008 (ZA) .................................. 200810426

(51) Int. Cl.
| | |
|---|---|
| *A61K 33/34* | (2006.01) |
| *A61K 33/04* | (2006.01) |
| *A61K 33/18* | (2006.01) |
| *A61K 33/24* | (2019.01) |
| *A61K 33/30* | (2006.01) |
| *A61K 33/32* | (2006.01) |
| *A61K 45/06* | (2006.01) |
| *A23K 20/20* | (2016.01) |
| *A23K 50/10* | (2016.01) |

(52) U.S. Cl.
CPC .............. *A61K 33/34* (2013.01); *A23K 20/30* (2016.05); *A23K 50/10* (2016.05); *A61K 33/04* (2013.01); *A61K 33/18* (2013.01); *A61K 33/24* (2013.01); *A61K 33/30* (2013.01); *A61K 33/32* (2013.01); *A61K 45/06* (2013.01); *A23V 2002/00* (2013.01)

(58) Field of Classification Search
CPC .... A61K 2300/00; A61K 33/04; A61K 33/30; A61K 33/32; A61K 33/34; A61K 33/24; A61K 33/00; A61K 33/26; A61K 31/28; A61K 33/18; A61K 45/06; A61K 31/00; A61K 9/0019; A61K 47/183; A61K 9/08; A61K 31/095; A61K 31/167; A61K 31/365; A61K 31/4184; A61K 31/429; A61K 39/00; A61K 47/02; Y10S 424/06; Y10S 514/836; A23V 2002/00; A23V 2250/1588; A23V 2250/1612; A23V 2250/1626; A23V 2250/1642; A23K 20/30; A23K 50/10; A23K 10/40; A23K 20/174; A23K 20/20; C09K 8/582
See application file for complete search history.

(56) References Cited

U.S. PATENT DOCUMENTS

| | | | | |
|---|---|---|---|---|
| 4,335,116 | A * | 6/1982 | Howard | A61K 31/315 424/630 |
| 6,872,723 | B2 * | 3/2005 | Frijlink | A61K 31/4709 514/253.06 |
| 7,285,292 | B2 * | 10/2007 | Laurie | A61K 31/28 424/630 |
| 8,231,910 | B2 * | 7/2012 | Laurie | A61K 9/0019 424/702 |
| 2005/0244511 | A1 * | 11/2005 | Laurie | A61K 31/28 424/630 |

OTHER PUBLICATIONS

Luo et al. (Environmental Pollution, 2006, vol. 144, pp. 862-871) (Year: 2006).*
wps.prenhall.com website (Factors that affect solubility, chapters 13 and 17), downloaded 2017 (Year: 2017).*
Luo et al. (Environmental Pollution, 2006, vol. 144, pp. 862-871). wps.prenhall.com website (Factors that affect solubility, chapters 13 and 17, downloaded in Oct. 2017).

* cited by examiner

*Primary Examiner* — Mark V Stevens
(74) *Attorney, Agent, or Firm* — Finnegan, Henderson, Farabow, Garrett & Dunner, LLP

(57) ABSTRACT

A trace element solution comprises at least the following metals: zinc; manganese; selenium; and copper; and which comprises a concentration of the metals of at least 90 mg/ml. The solution may comprise the following concentrations: at least 60 mg/ml zinc; at least 10 mg/ml manganese; at least 5 mg/ml selenium; and at least 15 mg/ml copper. The solution may comprise chromium, iodine and chromium.

11 Claims, No Drawings

TRACE ELEMENTS

CROSS-REFERENCE TO RELATED APPLICATIONS

This application is a continuation U.S. patent application Ser. No. 15/660,439, filed on Jul. 26, 2017, which is a divisional of U.S. patent application Ser. No. 13/130,336 filed on Aug. 4, 2011, as U.S. national stage of international patent application PCT/IB09/55402 filed on Nov. 30, 2009, The contents of the above-referenced applications are expressly incorporated herein by references to their entireties.

FIELD OF INVENTION

The present invention relates to trace elements.

BACKGROUND TO INVENTION

It has been found that there is a deficiency of certain trace elements in pastures for livestock in particular areas around the world. Various suggestions have been made to provide the required trace elements to such animals. Different chemical compounds and complexes have been investigated for applying the trace elements by way of licks, drenches or injections.

In general the problem with injectable solutions is that the concentrations of the minerals in the solutions is too low. This means that relatively large quantities have to be injected, which in turn causes tissue damage and also abscesses at the site of injection. Furthermore, it is generally the case that different trace elements seldomly are individually sufficient. This means that two or more trace element solutions have to be provided by way of separate injections.

ZA 1982/6778 (Laurie) discloses a trace element solution and a method of providing the trace elements to livestock. These trace element solution include ethylene diamino tetra acetic acid complex of the required mineral in suitable quantities. However, the trace element solution includes no selenium or selenite compound.

In the specification and claims the expression EDTA refers to ethylene diaminotetraacetic acid ($C_{10}H_{16}O_8N_2$ or $(HO_2CH_2C)_2NCH_2CH_2N-(CH_2CO_2H)_2$).

U.S. Pat. No. 4,335,116 (Howard) discloses mineral-containing therapeutic compositions containing EDTA complexes of trace elements. Notably, U.S. Pat. No. 4,335,116 utilises tetra-sodium EDTA, a selenium glycine complex, and metal chlorides for the preparation of the EDTA complexes. Unfortunately, the chloride ions cause contamination and each complex solution is to be made individually. Furthermore, overnight time is required for complexing and heating up afterward to speed up the process, requires extra apparatus. If mixtures are required, the individual solutions are to be blended. If various concentrations as well as compositions are to be made, it can only be done in a cumbersome way, requiring extra apparatus. A further problem arises when mixtures of high concentration are needed. In certain cases it would be impossible to deliver them, because mixing is always accompanied by dilution. The maximum concentration achieved with this method was 13.5 mg/ml.

U.S. Pat. No. 6,638,539 (Laurie et al) discloses a method of preparing a trace element solution, which includes the steps of providing at least one EDTA-complex, of providing a sodium selenite solution, and of combining the EDTA-complexes and the sodium selenite solution. However, the method enables production of a trace element solution of only about 55 mg/ml.

U.S. Pat. No. 7,285,292 (Laurie et al) discloses a trace element solution, which comprises at least one metal selected from the group comprising selenium, copper, zinc, manganese and chromium and which comprises a concentration of the metal(s) of at least 60 mg/ml. The solution further comprises at least one compound selected from the group comprising iodine, potassium iodide, sodium iodide, iron, iron chloride, zinc oxide, manganese sulphate, sodium selenite, copper carbonate, sodium carbonate, anhydrous disodium EDTA and sodium hydroxide. The trace element solution is prepared by a method consisting essentially of the steps of preparing a $MnCO_3$ mixture in a container; adding an EDTA/NaOH mixture to the container and subsequently adding at least one metal compound; and adding $Na_2SeO_3$ to the container to obtain the trace element solution. The method also comprises the step of adding $CrCl_3.6H_2O$ to the trace element solution.

Unfortunately the known solutions and methods therefore cannot provide solutions with suitable composition with high enough concentrations and sufficient ratios and sufficient concentrations of the various metals.

It is an object of the invention to suggest methods and means for overcoming these problems.

SUMMARY OF INVENTION

According to the invention, a trace element solution, which comprises at least the following metals:
(a) zinc;
(b) manganese;
(c) selenium; and
(d) copper,
and which comprises a concentration of the metals of at least 90 mg/ml.

Also according to the invention, a method of preparing a trace element solution comprising at least one metal selected from the group comprising zinc, manganese, selenium, and copper and comprising a concentration of the metals of at least 90 mg/ml, said method consisting essentially of the steps of:
(a) heating water;
(b) adding manganese carbonate to the water;
(c) adding zinc oxide to the water; and
(d) adding copper carbonate to the water to form a liquid mixture;
(e) adding a dry mixture comprising EDTA and/or EDDS and NaOH to the liquid mixture; and
(f) adding $Na_2SeO_3$ to form the trace element solution.

Yet further according to the invention, a trace element solution as prepared by the method as described herein.

Yet further according to the invention, a method of providing trace elements to animals, such as livestock, which comprises the steps of preparing a trace element solution as described herein and of providing the solution in a suitable quantity to an animal.

The method of preparing a trace element solution may be a continuous batch process.

The solution may comprise the following concentrations:
(a) at least 60 mg/ml zinc;
(b) at least 10 mg/ml manganese;
(c) at least 5 mg/ml selenium; and
(d) at least 15 mg/ml copper.

The solution may comprise chromium.
The solution may comprise iodine.

The solution may comprise at least 5 mg/ml chromium.
The solution may comprise at least 50-300 mg/ml iodine.
The ratio of zinc to manganese may be at least 2:1
The ratio of zinc to manganese may be at least 4:1
The ratio of zinc to copper may be at least 2:1 or 4:1
The ratio of zinc to selenium may be at least 4:1 or 12:1
The solution may comprise at least one compound selected from the group comprising chromium, iron, iodine, potassium iodide, sodium iodide, iron chloride, zinc oxide, manganese sulphate, manganese carbonate, sodium selenate, sodium selenite, copper carbonate, sodium carbonate, anhydrous disodium EDTA and sodium hydroxide.

At least one of the metal(s) may be provided in the form of an EDTA complex and/or an EDDS complex.

The EDTA source may be EDTA acid, disodium EDTA, tetra-sodium EDTA, calcium EDTA, potassium EDTA and/or any other EDTA source.

The solution may comprise chloro-cresol and/or benzyl alcohol as preservative.

The solution may be an injectable solution.
The solution may be a drenchable solution.
Step (a) may heat the water to 70 degrees Celsius.
The adding in step (e) may occur slowly to prevent excessive frothing.
The solution may be a clear blue solution.
The temperature of the solution may reach 100 degrees Celsius.
The solution may be allowed to cool.
The solution may after cooling have a temperature of 50 degrees Celsius.
Chloro-cresol may be added to the solution and stirred until dissolved.
The pH of the solution may be adjusted.
Water may be added to the solution.
The method may comprise the step of adding $CrCl_3 \cdot 6H_2O$ to the trace element solution.
The method may comprise the step of adjusting the pH of the trace element solution to 6.0 to 8.0
The method may comprise the step of adjusting the pH of the trace element solution by adding at least one compound selected from the group comprising NaOH and EDTA.
The trace element solution may be diluted.
The temperature of the $MnCO_3$ mixture may be at least 60 degrees Celsius.
Water having a temperature of at least 70 degrees Celsius may be added to the $MnCO_3$ mixture.
The addition of the EDTA/NaOH mixture may occur gradually with small quantities.
The method may comprise the step of cooling the trace element solution prior to addition of the $Na_2SeO_3$.
The $MnCO_3$ mixture may be obtained directly and/or prepared by mixing $MnSO_4$ and $Na_2CO_3$.
The metal compound may be selected from the group comprising ZnO, $CuCO_3$, $Na_2CO3$, $MnSO_4$ and $FeCl_3$.
The metal compound may be selected from the group comprising metal oxides, metal hydroxides and metal carbonates.

DESCRIPTION EXAMPLE

The invention will now be described by way of an example of injectable solutions in accordance with the invention.

The example relates to a method to prepare a trace element solution predominantly to be used for cattle and includes the mineral elements zinc, manganese, selenium and copper.

The method enables preparation of 25 liters of the solution containing at least 60 mg Zn, 10 mg Mn, 5 mg Se, and 15 mg Cu per ml.

In a 25 liter plastic container, water is heated to a temperature of 70 degrees Celsius so that the process can proceed at a temperature of at least 60 degrees Celsius.

0.556 Kilogram of manganese carbonate is added to the heated water whilst mixing.

1.890 Kilogram of zinc oxide is added to the mixture.

0.700 Kilogram of copper carbonate is added to the mixture slowly to form a liquid mixture.

In a separate container 10.17 kilogram EDTA and 2.70 kilogram of NaOH are mixed to form a dry mixture.

The dry mixture is slowly added to the liquid mixture to prevent excessive frothing and allow the reaction to complete and to leave a clear blue solution.

The temperature of the solution may reach 100 degrees Celsius and is allowed to cool to 50 degrees Celsius.

26.25 g of Chloro cresol is added to the solution and is stirred until dissolved.

The solution is then cooled to room temperature.

The recorded pH of the solution is now 4.656.

0.303 Kilogram of $Na_2SeO_3$ is added.

The recorded pH of the solution is now 5.115.

The pH is adjusted to 6.860 by adding a 50% NaOH solution.

The solution is now diluted with water to obtain the required weight, namely 1.300 kg/l.

The resultant trace element solution has a composition as follows:
(a) 60 mg/ml of zinc;
(b) 10 mg/ml manganese;
(c) 5 mg/ml selenium; and
(d) 15 mg/ml copper.

The invention therefore provides a trace element solution which is tissue friendly, i.e. is not damaging or irritant to the tissue of animals and which comprises zinc, manganese, selenium and copper and at a concentration of the metals of at least 90 mg/ml.

The trace elements in solution are in a scientifically formulated ratio according to the post-absorption requirements of the animals.

As an example the trace element solution comprises
(a) at least 60 mg/nil of zinc;
(b) at least 10 mg/ml manganese;
(c) at least 5 mg/ml selenium; and
(d) at least 15 mg/ml copper.

The solution may furthermore comprise at least 5 mg/ml chromium and at least 50-300 mg/ml iodine.

The method of preparing a trace element solution in accordance with the invention thus enables the production of a solution comprising an adequate trace mineral concentration so that a 5 to 10 milliliter injection can make a significant impact on the trace mineral status of the animal and an injection is provided at a rate of between 1 ml per 50 kg bodyweight (BW) and 1 ml per 100 kg BW, i.e. a practically applicable injectable supplement and a product that can improve the trace mineral status of an animal is provided. This is important as livestock producers will only inject livestock if a real benefit can be demonstrated. The subcutaneous injection is the preferred route to minimize tissue damage, but intra-muscular injection can also be used.

The invention claimed is:
1. A trace element aqueous injectable solution for veterinary use, comprising zinc, manganese, selenium, and copper, wherein the concentration of zinc ranges from 60 mg/ml up to a concentration that, in combination with said man- ganese, selenium, and copper, preserves the suitability for injection of the trace element aqueous injectable solution.

2. A trace element aqueous injectable solution for veterinary use according to claim 1, further comprising chromium, wherein the concentration of zinc ranges from 60 mg/ml up to a concentration that, in combination with manganese, selenium, copper, and chromium, preserves the suitability for injection of the trace element aqueous injectable solution.

3. A trace element aqueous injectable solution for veterinary use according to claim 1, wherein the concentration of manganese ranges from 10 mg/ml up to a concentration that, in combination with the concentration of the other metals, preserves the suitability of injection of the trace element aqueous injectable solution; the concentration of selenium ranges from 5 mg/ml up to a concentration of selenium that, in combination with the concentration of the other metals, preserves the suitability of injection of the trace element aqueous injectable solution; and the concentration of copper ranges from 15 mg/ml up to a concentration of copper that, in combination with the concentration of the other metals, preserves the suitability of injection of the trace element aqueous injectable solution.

4. A trace element aqueous injectable solution for veterinary use according to claim 3, further comprising chromium, wherein the concentration of chromium ranges from 5 mg/ml up to a concentration of chromium that, in combination with the concentration of the other metals, preserves the suitability for injection of the trace element aqueous injectable solution.

5. A trace element aqueous injectable solution for veterinary use according to claim 4, further comprising iodine, wherein the concentration of iodine in combination with the concentration of the metals preserves the suitability for injection of the trace element aqueous injectable solution.

6. A trace element aqueous injectable solution for veterinary use according to claim 5, wherein the concentration of iodine ranges from 50 mg/ml up to 300 mg/ml and wherein the concentration of iodine in combination with the concentration of the metals preserves the suitability for injection of the trace element aqueous injectable solution.

7. A method of providing a trace element aqueous injectable solution of claim 1 to a livestock animal comprising injecting the trace element aqueous injectable solution of claim 1 into the livestock animal.

8. A trace element aqueous injectable solution for veterinary use, comprising zinc, manganese, selenium, and copper, wherein the concentration of zinc is 60 mg/ml, the concentration of manganese is 10 mg/ml, the concentration of selenium is 5 mg/ml, and the concentration of copper is 15 mg/ml.

9. A trace element aqueous injectable solution for veterinary use of claim 8, further comprising chromium, wherein the concentration of chromium is 5 mg/l.

10. A trace element aqueous injectable solution for veterinary use of claim 9, further comprising iodine, wherein the concentration of iodine ranges from 50 mg/ml up to 300 mg/mi.

11. A method of providing a trace element aqueous injectable solution of claim 8 to a livestock animal comprising injecting the trace element aqueous injectable solution of claim 8 into the livestock animal.

* * * * *

UNITED STATES PATENT AND TRADEMARK OFFICE
CERTIFICATE OF CORRECTION

PATENT NO. : 10,350,241 B2
APPLICATION NO. : 15/968866
DATED : July 16, 2019
INVENTOR(S) : William Alfred Smith It is certified that error appears in the above-identified patent and that said Letters Patent is hereby corrected as shown below:

In the Claims

Claim 9, Column 6, Line 22, "5 mg/l", should read -- 5 mg/ml --.

Claim 10, Column 6, Lines 25-26, "300 mg/mi", should read -- 300 mg/ml --.

Signed and Sealed this
Nineteenth Day of November, 2019

Andrei Iancu
*Director of the United States Patent and Trademark Office*